United States Patent [19]

Hart et al.

[11] Patent Number: 4,956,278
[45] Date of Patent: Sep. 11, 1990

[54] ANAPLASMA MARGINALE ANTIGEN, ANTIGEN COMPOSITIONS, VACCINE AND PROCESS FOR THE PRODUCTION OF SAID ANTIGEN, ANTIGEN COMPOSITIONS AND VACCINE

[75] Inventors: Lewis T. Hart; Donald G. Luther; William J. Todd, all of Baton Rouge, La.

[73] Assignee: Louisiana State University, Baton Rouge, La.

[21] Appl. No.: 159,394

[22] Filed: Feb. 23, 1988

[51] Int. Cl.$^5$ .................... C12Q 1/24; C12P 21/00; C12N 1/00; C07K 3/12
[52] U.S. Cl. ..................... 435/30; 435/29; 435/41; 435/4; 435/71.1; 435/71.2; 435/243; 435/245; 435/258; 435/259; 435/261; 435/947; 435/808; 530/412; 530/414; 530/418; 530/420; 530/829
[58] Field of Search ............... 424/93, 88; 530/412, 530/418–420, 414, 829; 435/68, 30, 947, 29, 41, 4, 71.1, 71.2, 243, 245, 258–259, 261, 808

[56] References Cited

U.S. PATENT DOCUMENTS 4,329,331  5/1982  Kallick ........................... 424/88

FOREIGN PATENT DOCUMENTS 8300017  1/1983  PCT Int'l Appl. .
8401897  5/1984  PCT Int'l Appl. .

OTHER PUBLICATIONS

Palmer, *Inf. and Imm.*, vol. 50(3) 1985, pp. 881–886.
Barbet et al, *Inf. and Immunity*, 1983, vol. 40, pp. 1068–1074.
Kuttler et al, *Vet Microbiol.*, 9(2) 1984, pp. 181–186.
S. McCorkle-Shirley, MS: L. T. Hart, PhD; A. D. Larson, PhD; W. J. Todd, PhD; J. Donovan Myhand, MS, High-Yield Preparation of Purified *Anaplasma Marginale* from Infected Bovine Red Blood Cells; Aug. 1985, pp. 1745–1747, American Journal of Veterinary Research, vol. 46, No. 8.
D. Gene Luther; Lewis T. Hart; W. J. Todd; Ron Byford Anaplasmosis Vaccines for Cattle; Jul. 1987, pp. 4–5, The Louisiana Cattleman vol. 20, No. 7.
Susan Looney, W. J. Todd, L. T. Hart, Nell Morris, The Immune Response of the Bovine to Purified Anaplasma Marginale, Mar. 1987; p. 117, American Society for Microbiology, Abstracts of the Annual Meeting, 1987 E-84.
D. G. Luther, L. T. Hart, W. J. Todd, R. L. Byford, Bovine Anaplasmosis: Current and Future Treatments, 1985, pp. 10–11, Louisiana Agriculture, vol. 29 #1.
T. E. Amerault, A Review of the Card Test for Anaplasmosis, Mar. 19, 20, 1973, pp. 133–135, Proceedings of the Sixth National Anaplasmosis Conference.
S. Montenegro-James, M. Toro, E. Leon, B. K. Baek, A. T. Guillen, M. Ristic, Induction of Protective Immunity Against Bovine Anaplasmosis with Purified, Nonviable Anaplasma Marginale, Organisms, Nov. 29–Dec. 3, 1987, p. 78, The 36th Annual Meeting of the American Society of Tropical Medicine and Hygiene.
Guy H. Palmer, Travis C. McGuire, Immune Serum Against Anaplasma Marginale Initial Bodies Neutralizes Infectivity for Cattle; Aug. 1984, pp. 1010–1015, The Journal of Immunology, vol. 133, No. 2.
S. A. Ferenc, C. H. Courtney, M. J. Burridge, Trypanosoma Vivax in the Caribbean Basin, Nov. 29–Dec. 3, 1987, p. 78, The 36th Annual Meeting of the American Society of Tropical Medicine and Hygiene.

*Primary Examiner*—Garnette Draper
*Attorney, Agent, or Firm*—Llewellyn A. Proctor

[57] ABSTRACT

Anaplasma marginale antigen, antigen compositions, vaccine and process for the production of said antigen, antigen composition and vaccine are disclosed. The Anaplasma marginale is free of the erythrocyte antigens that cause neonatal isoerythrolysis, and effective as a vaccinate which will not only protect the vaccinate against bovine anaplasmosis, but does not induce neonatal isoerythrolysis in offspring of vaccinates.

10 Claims, No Drawings

ANAPLASMA MARGINALE ANTIGEN, ANTIGEN COMPOSITIONS, VACCINE AND PROCESS FOR THE PRODUCTION OF SAID ANTIGEN, ANTIGEN COMPOSITIONS AND VACCINE

FIELD OF THE INVENTION

This invention relates to a process for the preparation of an antigen, and vaccine for anaplasmosis. In particular, it relates to the production of *Anaplasma marginale* which is free of erythrocyte antigens.

BACKGROUND

The 8th edition of *Bergy's Manual of Determinative Bacteriology* places *Anaplasma marginale* in Order Rickettsiales, Family Anaplasmatceae and genus Anaplasma. This intraerythrocytic parasite occurs in association with bovine erythrocytes.

Anaplasmosis, a hemolytic disease of the bovine caused by the blood parasite *Anaplasma marginale*, has caused major economic losses to diaryman and ranchers. It is an endemic problem that can flare up to epidemic proportions at any time. *A. marginale* parasitizes bovine red blood cells (RBC) and destroys them, this leading to hemolytic anemia which may cause death, particularly in adult cattle. Cattle which do not die can become carriers of the disease for life, unless properly treated. Efforts have been made to produce a vaccine for anaplasmosis, and a known, currently marketed, vaccine effectively prevents clinical disease in vaccinates; reducing death losses from acute anaplasmosis to almost zero. However, that vaccine is grossly contaminated with bovine RBC fragments, or RBC antigens, which can cause fatal neonatal isoerythrolysis (NI) in the offspring of vaccinated cows. It has been found as a result of experimental work, that the process used to separate the *A. marginale* from the RBC to prepare the commercial vaccine leaves portions of the RBC contaminated with the organisms. As a consequence, when injected into cattle, the animal not only makes antibodies for the *A. marginale* but, if the blood type of the cow and that of the vaccine are different, antibodies for the RBC are also made by the cow. This does not adversely affect the health of the cow that has received the vaccine, but it causes the concentration of antibodies against some types of RBC in her colostrum. If the blood type of the nursed calf is the same as the RBC in the vaccine, the colostrum will be loaded with antibodies against the calf's RBC. These antibodies will destroy the calf's RBC, and the calf will die. As a result of this condition, known as neonatal isoerythorlysis, NI, many cattlemen have discontinued the use of this vaccine in their cows. Thus, there exists a pressing need for an improved antigen, and vaccine for the suppression of anaplasmosis, particularly an antigen and vaccine free of erythrocyte antigens that cause NI, and process for the preparation of said antigen, and vaccine.

OBJECTS

It is, accordingly, the primary objective of this invention to supply these needs In particular, it is an object of this invention, to provide a process for the separation of *A. marginale* and host red blood cells, RBC, and use of the separated, purified *A. marginale* and vaccine for anaplasmosis, particularly an antigen and vaccine which will not produce neonatal isoerythrolysis, NI, in offspring of the vaccinate.

A more specific object is to provide a process for obtaining purified *A. marginale* in high yield from infected bovine RBC, particularly one which is relatively simple, inexpensive, and which lends itself to large scale production.

Another object is to provide *A. marginale* sufficiently pure of host red blood cells, RBC, that it can be directly employed in a vaccine preparation to prevent anaplasmosis, and which will not produce anti-RBC antibodies responsible for neonatal isoerythrolysis, NI, in offspring of the vaccinate.

Yet another object is to provide an antigen, and vaccine sufficiently pure that, when injected, it will prevent anaplasmosis, and not produce the anti-RBC antibodies responsible for neonatal isoerythrolysis, NI, in offspring of the vaccinate.

THE INVENTION

These objects and others are achieved by a process for separating from *A. marginale* infected erythrocytes, particularly *A. marginale* infected bovine erythrocytes, an *A. marginale* free of erythrocyte antigens that cause NI. A lysing agent, preferably ammonium chloride, is employed to selectively lyse the erythrocytes without lysing the white blood cells, this permitting subsequent removal of the white blood cells by low speed centrifugation Subsequent high speed centrifugation will thus yield a pellet of *A. marginale* and lysed erythrocytes, or erythrocyte ghosts, free or substantially free of white blood cells, and nucleic acids found in the leukocytes, or white blood cells. The *A. marginale* infected erythrocyte ghosts are fractionated under pressure, suitably at pressure above about 2000 pounds per square inch (psi), to fragment the erythrocyte ghosts and release therefrom *A. marginale. A. marginale* are released as individual particles, often called initial bodies because they can initiate a new round of infection. The *A. marginale* initial bodies are then purified over a substance of density slightly greater than that of the *A. marginale*, suitably Renografin (a Trademark of Squibb, New Brunswick, N.J. 08903; Diatrizoate Meglumine and Diatrizoate Sodium Injection USP), or sucrose solution, and the material produced is then washed free of the Renografin to produce a highly purified *A. marginale*, notably one free of host erythrocyte antigens that cause NI. The purified *A. marginale* is antigenic and can be used as a vaccine for anaplasmosis. The protection afforded vaccinates against anaplasmosis results from the presence of *A. marginale*, or anaplasma cell, contained in the vaccine preparation. Separation of the RBC antigen from the *A. marginale* provides an effective vaccine for anaplasmosis but one which will not induce NI in the calves of the vaccinates.

A preferred process for the preparation of pure *A. marginale*, and vaccine prepared from said *A. marginale*, is described as follows:

(1.) The purified *A. marginale* needed for a vaccine is obtained from anaplasmosis-infected bovine red blood cells, suitably from a source wherein the parasitized bovine red blood cells are present in high concentration. A high parasitemia is induced in the blood of a cow by innoculation of *A. marginale* into the blood.

(2.) The infected cow is exanguinated, preferably when the parasitemia is at its peak. The blood is collected into an anticoagulant, suitably into Alsever's solution. Exanguination is preferably carried out when the percentage of parasitized erythrocytes has reached about 40% to about 90%.

(3.) Erythrocytes, or RBC, infected with *A. marginale* are separated from the plasma and coagulant, preferably by centrifugation. Centrifugation, at low speed, i.e., at about 1000 ×g for 20 minutes, sediments a pellet of the infected erythrocytes, and produces stratification above the pellet of a supernatant fluid, as well as the formation of a buffy coat of white blood cells. The supernatant fluid and buffy coat of white blood cells formed at the top of the pellet are removed by aspiration, or suction vacuuming, and discarded. The pellet of *A. marginale* infected RBC is washed several times, generally two or three times, with a balanced salt solution, suitably a phosphate buffered saline (PBS) solution, or other balanced salt solution.

(4.) The washed erythrocytes are lysed by resuspending the pellet in a hypotonic liquid, or solution, suitably in three volumes of an 0.85% ammonium chloride solution (at 4° C.), or treated by osmotic lysis with constant stirring using hypotonic solutions, preferably the former. Selective lysing of the erythrocytes in this manner leaves the leukocytes intact. Proteases are inhibited, suitably by adding 1 mM phenylmethylsulfonyl fluoride (PMSF).

(5.) The remaining intact leukocytes, or white blood cells, are removed after lysis of the erythrocytes by pelleting, by centrifuging e.g., at low speed, at 1,060 × to about 1,300 ×g for 15 minutes. The pelleted leukocytes are then discarded. The removal of the leukocytes eliminate a source of nucleic acids contamination from the final *A. marginale* preparation. The leukocyte nucleic acids are sticky and if not removed would cause contamination of the vaccine preparation by binding to potential NI antigens. The supernatant contains *A. marginale* infected erythrocyte ghosts, or lysed erythrocytes.

(6.) The lysed erythrocytes and *A. marginale* are concentrated by high speed centrifugation, suitably at about 18,000 ×g for ten minutes. In concentrating the lysed erythrocytes the supernatant fluid is discarded, and suitably the pelleted material is pooled and resuspended in PBS, generally a volume of PBS equal to about one-half the volume of packed erythorcytes originally lysed with ammonium chloride. A final concentration of 1 mM PMSF is generally added to the suspension.

(7.) The pellet from step "6" is resuspended in PBS and sufficient pressure applied to remove the *A. marginale* from the erythrocyte ghosts Generally, the PBS is added to the pellet in an amount equal to about 1.5 times the pellet volume in Step 4 and pressurized, suitably by passage through a French Pressure Cell and from about 1500 pounds per square inch (psi) to about 2500 psi is applied to disrupt the erythrocytic membranes and disassociate intact initial bodies from the *A. marginale* body. The *A. marginale* is thus separated from the erythrocyte ghosts.

(8.) The *A. marginale* is again concentrated by centrifugation, suitably at low speeds, e.g., at about 9,400 ×g for 45 minutes, over a density cushion, generally about 40% Renografin, or other solution forming a cushion of similar density, e.g., sucrose. The *A. marginale* forms a concentrated band at the interface of the pressure cell lysate and the density cushion.

(9.) The *A. marginale* at the interface is harvested by aspiration. The *A. marginale* is washed by repeated centrifugation, suitably at 18,000 ×g, and the *A. marginale* then resuspended in PBS.

The *A. marginale* is inactivated for vaccine use by various known techniques, suitably by treatment with formaldehyde in water ($HCHO:H_2O$) at concentration of from about 1:1000 to about 5:100, or about 2:100 to about 4:100, over a period of from about 24 to about 120 hours. Temperature is not critical, but low heat may be used Suitably, e.g., formation at a concentration of about 1;100 for about 72 hours at a temperature of about 30° C. to about 40° C. will inactivate the pathogen.

The *A. marginale* antigen optionally may be adsorbed on alum to increase its immunogenicity and may be administered with other adjuvants, inclusive of aqueous and non-aqueous vehicles.

The *A. marginale* is immunogenic to susceptible species, notably bovines, at a dosage level generally of from about 10 micrograms to about 20 micrograms, protein per milliliter (ml) of liquid, preferably from about 12 micrograms to about 15 micrograms of protein, per ml of vehicle, suitably as determined by the Lowery method.

The following non-limiting examples are further illustrative of the invention, and specifically defines a preferred technique for the production of *A. marginale* free of erythrocyte antigens. In preparation of a vaccine from the purified antigen, an adjuvant is added, and the vaccine dosage level is adjusted between about 10 and 20 micrograms protein, per ml of liquid as determined by in vivo vaccination, and experimental challenge. The protein level in the dosage is determined by the Lowery method

EXAMPLES

A cow was infected with *A. marginale* (Mississippi strain) by transfusion of the animal with 50 ml of heparinized blood drawn from an *A. marginale* carrier animal.

Hematology

Examination and enumeration of erythrocytes infected with *A. marginale* was accomplished by monitoring the packed cell volume (PCV) as determined by the microhematocrit method (Donovan-Myhand, J., L. T. Hart, C. L. Liu, C. Ohrberg and C. Seger, 1984. A rapid straining procedure for *A. marginale* in bovine erythrocytes. A. J. Vet. Res. 45: 2143–2144). The percentage of parasitized erythrocytes (PPE) was determined by microscopic examination of Diff-Quik (American Scientific Products, McGaw Park, Ill.) stained blood smears.

When the PPE reached 40–60%, the animal was anesthetized and exanguinated. Exanguination was done via the jugular vein with the aid of a hand operated vacuum pump. The blood was collected into an equal volume of sterile Alsevar's solution (116 mM Dextrose; 27 mM sodium citrate dihydrate; 2.62 mM citric acid monohydrate; and 71 mM sodium chloride) at pH 6.7.

Preparation of Pure *A. Marginale*

Erythrocytes infected with *A. marginale* were separated from the plasma and Alsevar's solution by centrifugation at 1,060 ×g for 20 minutes. The supernatant fluid and buffy coat were removed by aspiration. The cells were pooled and washed three times in phosphate buffered saline (2.7 mM potassium choloride; 7.6 mM sodium phosphate dibasic; 1.9 mM potassium phosphate monobasic; and 86 mM sodium chloride) at pH 7.4 (PBS). The erythrocytes were sedimented at 1060 ×g for 20 minutes.

After the final wash, the volume of packed erythrocytes was noted and the cells were resuspended in 3 volumes of cold (4° C.) 0.83% ammonium chloride and incubated at room temperature with constant stirring for 10 minutes. Inhibition of possible protease activity released by cell lysis was accomplished by addition of 1 mM phenylmethylsulfonyl fluoride (PMSF) to the lysate. After lysis, the suspension was centrifuged at 1,300 ×g in a Beckman TJ-6 centrifuge equipped with a swinging bucket rotor for 15 minutes to remove intact leukocytes. The pelleted leukocytes were discarded and the supernatant, which contained *A. marginale* infected erythrocyte ghosts were centrifuged at 18,500 ×g for 10 minutes in a fixed angle rotor in a Sorvall RC-5B centrifuge. The supernatant fluid was discarded and the pelleted material was pooled and resuspended in PBS A final concentration of 1 mM PMSF was again added to the suspension.

The use of ammonium chloride to selectively lyse red blood cells in this manner allows for the removal of intact leukocytes with the low speed centrifugation. Centrifugation at this force does not sediment RBC ghosts or *A. marginale*. The removal of leukocytes eliminates the nucleic acids as a source which can contaminate initial *A. marginale* preparations prepared by this procedure. Thin smears of the *A. marginale* preparation stained with acridine orange revealed no extraneous nucleic acids contaminating the preparation.

The suspension containing the *A. marginale* lysed erythrocytes was next passed through a Sorval French Pressure Cell Fractionator equipped with a Ribi valve at 2,000 pounds per square inch (psi) at a flow rate of approximately 500 ml per hour. The effluent from the cell fractionator was distributed into 40 ml centrifuge tubes and underlayed with 40% Renografin (37% organically bound iodine; Squibb Diagnostics, New Brunswick, N.J.) in PBS and were centrifuged at 9,400 ×g for 45 minutes in a Sorval HS-4 rotor in a Sorval RC-5B centrifuge. The *A. marginale* migrated to just below the lysate-Renografin interface. The lysate was aspirated to just above the interface The remaining Renografin and *A. marginale* were pooled and diluted 1:4 (v/v) with PBS and centrifuged at 1,300 ×g for 15 minutes in a Beckman TJ-6 centrifuge. Sedimented material was discarded and the supernatant was centrifuged at 10,000 ×g for 20 minutes in a fixed angle rotor in a Sorval RC-5B centrifuge. The pelleted *A. marginale* were washed 2 times in PBS by centrifugation at 10,000 ×g for 10 minutes. The final pellet of *A. marginale* was resuspended in PBS and stored at −80° C. for use as a vaccine.

Passage of the erythrocyte lysate suspension through the french pressure cell disrupts the erythrocytic membranes and disassociates intact initial bodies from the *A. marginale* inclusion or marginal body. After centrifugation of the suspension over Renografin, the *A. marginale* initial bodies band immediately below the lysate-Renografin interface. The supernatant is readily removed by aspiration and the Renografin, which contains the *A. marginale* initial bodies, is easily collected by decantation.

Vaccine Preparation and Trial

The *A. marginale*, or RBC parasites, separated from bovine RBC, as described, was taken from storage, made into a vaccine and compared with the known commercial vaccine in an experimental vaccine trial for anaplasmosis. The separated *A. marginale*, or RBC parasites, were killed and emulsified in an adjuvant and injected into an anaplasmosis-free yearling. For this study, one yearling was vaccinated with the purified preparation. One yearling was vaccinated with the commercial vaccine and one yearling, not vaccinated, served as a positive control for the experiment. Four weeks later, another set of similar injections was administered to the same yearlings.

Twenty-two days later each yearling was challenged by an intravenous injection of 0.1 ml of blood from anaplasmosis carrier. Periodically, blood samples were taken for 106 days after vaccination. The number of RBC in each blood sample was determined, and each blood sample was stained and microscopically examined for *A. marginale*-infected RBC. For the same period of time, serum samples were obtained and stored frozen. After all serum samples were collected, they were analyzed for anti-*A. marginale* antibodies by an enzyme linked immunospecific assay (ELISA) test, a sensitive laboratory test that measures antibodies in bovine serum that react with *A. marginale*.

The yearling vaccinated with purified *A. marginale* had a loss of RBC which paralleled that of the yearling vaccinated with the commercial vaccine. Both vaccinated yearlings lost 21 percent of their RBC, compared to a 64 percent loss for the unvaccinated control.

TABLE

Antibody response to vaccination in yearlings prior to challenge with virulent *A. marginale* and percent red blood cell volume and percent *A. marginale*-infected red blood cells following challenge.

| Yearling Number | Vaccine used | Lowest PCV[1] | Loss of RBC[2] | Highest parasitemia[3] | Highest ELISA reading[4] |
|---|---|---|---|---|---|
| | | | | Percent | |
| 21 | Commercial | 22 | 21 | 2.3 | 1.8 |
| 22 | Separated A. Marginale | 23 | 21 | 2.2 | 1.8 |
| 23 | None | 11 | 64 | 22.8 | 0.5 |

[1]Packed cell volume. Figure represents volume of red blood cells in the blood.
[2]Percent loss of RBC was calculated by dividing red blood cell volume at its lowest value by red blood cell volume at challenge and multiplying by 100.
[3]Percent parasitemia was determined by microscopic examination of stained blood smears.
[4]The ELISA reading is optical density and is logarithmic ($Log_{10}$). An increase in the ELISA reading indicates the antibody level has increased. The ELISA reading on day of challenge was 1.7, 1.5 an 0.14 for yearlings 21, 22 and 23 respectively.

Both had a low percentage of infected RBC (2.3 and 2.2 percent). The nonvaccinated yearling lost 64 percent of his RBC, and 22.8 percent of his RBC were parasitized at maximum. Yearlings receiving the commercial vaccine and the purified *A. marginale* produced high levels of anti-*A. marginale* antibody after vaccination and subsequent booster vaccination. The nonvaccinated yearling mounted a weak antibody response after challenge, which reached a maximum immediately prior to its development of acute anaplasmosis. Neither vaccinated yearling had external clinical signs of anaplasmosis.

These results with purified *A. marginale* show that separation of *A. marginale* from infected bovine RBC does not alter its effectiveness as a vaccine for anaplasmosis. The measurement of anti-*A. marginale* antibody induced in a yearling after vaccination with killed organisms and subsequent challenge with anaplasmosis carrier blood shows that high levels of specific antibodies are formed in response to vaccination. Although a high level of anti-*A. marginale* antibody does not prevent anaplasmosis, it does prevent the development of acute disease.

The success in separating intact *A. marginale* from infected bovine blood provides a vaccine that yields a level of protection unsurpassed by that of the commercially available vaccine, but without the fragments of cattle RBC that can lead to NI. Western blots using serum from experimentally vaccinated cows reacted strongly with *A. marginale* but not with bovine erythrocytes.

Having described the invention, what is claimed is:

1. A process for obtaining from *Anaplasma marginale* infected erythrocytes, and leukocytes, *Anaplasma marginale* sufficiently pure for use in a vaccine which, on injection, is effective in protecting the vaccinate against anaplasmosis and does not induce neonatal isoerythrolysis in offspring of the vaccinate which comprises selectively lysing the erythrocytes of the *Anaplasma marginale* infected erythrocytes with a lysing agent, without lysing the leukocytes, concentrating the *Anaplasma marginale* and lysed erythrocytes, while separating leukocytes therefrom, subjecting the concentrate of *Anaplasma marginale* and erythrocytes, from which the leukocytes have been separated, to fractionation under pressure to release therefrom *Anaplasma marginale* initial bodies, concentrating the *Anaplasma marginale* initial bodies by centrifugation over a density cushion so that the *Anaplasma marginale* initial bodies become concentrated in a band adjacent said density cushion, harvesting the *Anaplasma marginale* initial bodies, and washing the *Anaplasma marginale* initial bodies to obtain substantially pure *Anaplasma marginale*.

2. The process of claim 1 wherein the erythrocytes of the *Anaplasma marginale* are selectively lysed with an ammonium chloride solution, 3. The process of claim 1 wherein the *Anaplasma marginale* and lysed erythrocytes are separated from the leukocytes by centrifugation.

4. The process of claim 1 wherein the *Anaplasma marginale* and lysed erythrocytes, from which the leukocytes have been separated, and subjected to fractionation under pressure in the presence of a density cushion, is subjected to pressure in excess of 1500 psi.

5. The process of claim 4 wherein the applied pressure ranges from about 1500 psi to about 2500 psi.

6. The process of claim 1 wherein the density cushion over which the *Anaplasma marginale* and lysed erythrocytes subjected to pressure to fragment the lysed erythrocytes and release therefrom *Anaplasma marginale* initial bodies is about 40 percent Renografin or solution of similar density.

7. The process of claim 6 wherein the *Anaplasma marginale* initial bodies and lysed erythrocytes form as a concentrated band at the interface of the lysate and the Renografin, and this interface is separated by aspiration.

8. The process of claim 1 wherein the source of *Anaplasma marginale* infected erythrocytes, and leukocytes, is bovine in which a high parasitemia is induced by inoculation of *Anaplasma marginale* into the blood, and the blood of the injected bovine exanguinated and collected in an anticoagulant.

9. The process of claim 8 wherein the parasitema, as measured by the percentage of parasitized erythrocytes ranges from about 40 percent to about 90 percent.

10. A process for preparation of *Anaplasma marginale* free of erythrocyte antigens that cause neonatal isoerythrolysis, suitable as a vaccine which, on injection, will protect the vaccinate against anaplasmosis without inducing neonatal isoerythrolysis in offspring of the vaccinate which comprises inducing a parasitemia in bovine by inoculation of *Anaplasma marginale* into the blood, exanguinating the infected bovine when the parasitema is at about its peak, and collecting the blood with an anticoagulant, pelletizing by centrifugation the *Anaplasma marginale* infected erythrocytes in saline, and separating said pellet from a supernatant liquid and buffy coat of leukocytes formed by the centrifugation, lysing the erythrocytes of the separated *Anaplasma marginale* infected erythrocytes, and residual leukocytes, by contact with a solution of ammonium chloride, removing the remaining leukocytes from the lysed erythrocytes and *Anaplasma marginale* by centrifugation, concentrating the lysed erythrocytes and *Anaplasma marginale* from which the leukocytes have been separated by centrifugation, subjecting the lysed erythrocytes and *Anaplasma marginale* to fractionation under pressure to release therefrom *Anaplasma marginale* initial bodies, concentrating the *Anaplasma marginale* initial bodies by centrifugation over a density cushion so that the *Anaplasma marginale* initial bodies concentrate as a band adjacent said density cushion, separating the band in which the *Anaplasma marginale* initial bodies are concentrated, and washing the separated band in which the *Anaplasma marginale* initial bodies are concentrated to produce *Anaplasma marginale* which is substantially free of erythrocyte antigens.

* * * * *